United States Patent [19]

Loucks, Sr., deceased et al.

[11] Patent Number: 4,701,471
[45] Date of Patent: Oct. 20, 1987

[54] SKIN CARE COMPOSITION

[76] Inventors: Joseph Loucks, Sr., deceased, late of 915 S. Center St., No. 11; by Joseph Loucks, Jr., executor, 325 S. Henry, both of Geneseo, Ill. 61254

[21] Appl. No.: 852,419

[22] Filed: Apr. 16, 1986

[51] Int. Cl.$^4$ .............................................. A61K 7/48
[52] U.S. Cl. .................................. 514/847; 514/861; 514/887
[58] Field of Search ................... 514/78, 558, 844, 847

[56] References Cited

U.S. PATENT DOCUMENTS

| | | | |
|---|---|---|---|
| 3,959,491 | 5/1976 | Young et al. | 514/844 |
| 4,406,884 | 9/1983 | Fawzi et al. | 514/558 |
| 4,427,670 | 1/1984 | Ofuchi et al. | 514/78 |

OTHER PUBLICATIONS

Chemical Abstracts, 1984, vol. 100, pp. 39455k, Nippon Oils and pp. 39461j, Shiseido.
Chemical Abstracts, 1982, vol. 92, pp. 185717e, Delbene.

Primary Examiner—Dale R. Ore

[57] ABSTRACT

A cosmetic and pharmaceutical composition in the form of non-aqueous antimicrobial creams, lotions, and gels for topical application to the skin comprises bovine bone marrow acids mixed with lecithin for prevention of the fatty acid oxidation and odor putrefaction. The preparation of this product is accomplished without the use or incorporation of any inorganic chemicals, petroleum products, additional water. The heat treated solution provides relief for dry, flaky, and itchy skin and particularly for non-specific dermatitis and rashes.

6 Claims, No Drawings

SKIN CARE COMPOSITION

BACKGROUND OF THE INVENTION

This invention pertains to skin care products and more particularly to compositions which reduce the dryness or flakiness of skin and provide a relief of non-specific dermatitis and rashes.

This invention relates to an effective treatment for a dry, flaky and relatively inflexible skin.

Human skin should be soft, supple and flexible both for healthy functioning of the epidermis and for cosmetic purposes. The stratum corneum, which is the outer layer of the epidermis may become dry and flaky when exposed to some climatic conditions, detergents solvents, or the like. As a result, skin moisture may be lost along with desired soft, supple, and flexible characteristics. There has been only a limited amount of success when attempts have been made to apply topically fats, emollients, phospholipids, or sterols to the skin in order to treat dryness. Moreover, these treatments are not particularly useful because they are generally lost when the skin is washed.

Accordingly, an object of this invention is to provide new and improved topical, anti-microbial compositions in the form of lotions or creams which do not contain inorganic chemicals or petroleum products. Another object is to provide a process for preparing a cosmetically acceptable composition.

The inventive process includes the extraction of the basic ingredients by heat and filtration. Accordingly, there are no inorganic chemicals in the finished product. The invention does use an oleic acid and a palmitic acid, which are derived by an extraction of fatty acids and esters. Stearic acid, low molecular weight fatty acids, and lauric acid are obtained by filtration. Myristic, cis-9-palmitoleic, and linoleic acids are derived by an emulsification to produce the fatty acids in smaller globule sizes. Cis-a-palmitoleic acid is a known acid which is described in an Organic Chemistry book entitled "Organic Chemistry, Second Edition" by T. W. Graham Solomons, published in New York, U.S.A. by John Wiley & Sons publishers.

The composition preparation process begins with sawing large bovine bones along the longitudinal center plane to cut them into halves. The bone marrow is then scraped or scratched from the halves and placed into a heating vessel. Next, the marrow should be heated to its boiling point for a period which is long enough to melt it into a liquid. The resulting substance is then strained through a fine filter paper, perhaps as fine as a toilet tissue, in order to remove all solids and to retain only the liquefied material. The filter paper is supported by a metal screen of relatively fine mesh. The extraction of the basic ingredients from bone marrow by heat and filtration, rather than by the use of chemical solvents, precludes the presence of any inorganic chemicals in the finished product.

However, without an emulsifier and an antioxidant the bone marrow liquid material is greasy and may not penetrate the skin. Also, it would oxidize in a warm environment.

Therefore, a purely organic form of lecithin is thoroughly blended (preferably in a blender) into the hot liquid of the marrow to assure a complete emulsification and distribution of its antioxidant properties. Lecithin is derived from soybeans and is one of the best surface emulsifiers and antioxidants. Lecithin breaks down the large fatty acid globules into tiny globules which will remain in a homogeneous mixture and will not separate when in a solution. Separation would otherwise occur within about one minute and at the temperature of approximately 212° F. The lecithin antioxidant action provides for preservation and prevention of rancidity, and a putrifying odor which would otherwise result from an oxidation of the fatty acids. Lecithin should not be used alone as a skin creme.

Pure lemon oil is blended into this solution in order to give it a pleasing fragrance which is organic in origin. Lemon oil should not be used by itself as a skin lotion.

The blended solution is cooled down in its final container to a temperature lower than 85° Fahrenheit, which is approximately the temperature at which the solution will melt. The melting point temperature must be below the body temperature of 98.6° Fahrenheit but above the room temperature. The level of emulsification can be regulated by using a selected volume or percentage of the emulsifier.

The skin care product prepared according to the above described method does away with petroleum products, inorganic chemicals and any addition of water. The percentage of the combined constituents is important for a successful use of the composition.

The present invention is illustrated in the following example.

EXAMPLE

According to the invention, skin care composition is prepared in the form of a non-aqueous cream, by mixing the following ingredients:

| INGREDIENTS | PERCENTAGE |
| --- | --- |
| Oleic Acid | 42.00 |
| Palmitic Acid | 29.00 |
| Stearic Acid | 20.00 |
| Myristic Acid | 3.00 |
| Cis -9- Palmitoleic Acid | 2.00 |
| Linoleic Acid | 2.00 |
| Low Molecular wt. Fatty Acids & Esters | 1.34 |
| Linolenic Acid | .50 |
| Lauric Acid | .10 |
| Emulsifier and Antioxidant (Lecithin) | .03 |
| Fragrance | .03 |

The skin cream relieves dry, flaky, or itchy skin and helps fine wrinkles. Its antimicrobial qualities are also particularly helpful for relief of non-specific dermatitis and rashes.

Those who are skilled in the art will readily perceive how to modify the invention. Therefore, the appended claims are to be construed to cover all equivalent structures which fall within the true scope and spirit of the invention.

What is claimed is:

1. A non-aqueous moisturizing skin care composition in the form of a topical preparation, said composition comprising approximately 42% by weight of oleic acid, and approximately 2% by weight of an emulsifier selected from the group consisting of lecithin, a palmitic acid, a stearic acid, a myristic acid, and a cis-9-palmitoleic acid.

2. The composition according to claim 1, wherein the emulsifier includes 29% by weight of a palmitic acid, 20% by weight of a stearic acid and 3% by weight of a myristic acid.

3. The composition according to claim 1, wherein the emulsifier further includes 21% by weight of a linoleic acid.

4. The composition according to claim 1, wherein the emulsifier further includes 21% by weight of a lecithin.

5. A method for moisturizing dry skin, said method comprising the topical application to the affected situs of an effective amount of composition according to claim 1.

6. A non-aqueous moisturizing skin cream composition having the following ingredients:

| INGREDIENTS | PERCENTAGE |
|---|---|
| Oleic Acid | 42.00 |
| Palmitic Acid | 29.00 |
| Stearic Acid | 20.00 |
| Myristic Acid | 3.00 |
| Cis -9- Palmitoleic Acid | 2.00 |
| Linoleic Acid | 2.00 |
| [Low Molecular wt. Fatty Acids & Esters | 1.34] |
| Linolenic Acid | .50 |
| Lauric Acid | .10 |
| Emulsifier and Antioxidant (Lecithin) | .03 |
| Fragrance | .03 |

* * * * *